US010792644B2

(12) United States Patent
Cadran et al.

(10) Patent No.: US 10,792,644 B2
(45) Date of Patent: Oct. 6, 2020

(54) CATALYST TA-NB FOR THE PRODUCTION OF 1,3-BUTADIENE

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Nicolas Cadran, Oullins (FR); Alexandra Chaumonnot, Lyons (FR)

(73) Assignees: IFP Energies nouvelles, Rueil-Malmaison (FR); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 0 days.

(21) Appl. No.: 15/744,386
(22) PCT Filed: Jul. 5, 2016
(86) PCT No.: PCT/EP2016/065824
§ 371 (c)(1),
(2) Date: Jan. 12, 2018
(87) PCT Pub. No.: WO2017/009108
PCT Pub. Date: Jan. 19, 2017

(65) Prior Publication Data
US 2018/0200696 A1 Jul. 19, 2018

(30) Foreign Application Priority Data
Jul. 13, 2015 (FR) .................................... 15 56661

(51) Int. Cl.
B01J 23/20 (2006.01)
B01J 37/02 (2006.01)
B01J 35/10 (2006.01)
C07C 1/20 (2006.01)
B01J 37/03 (2006.01)
B01J 21/08 (2006.01)
B01J 37/10 (2006.01)
B01J 37/08 (2006.01)

(52) U.S. Cl.
CPC ........... B01J 23/20 (2013.01); B01J 35/1019 (2013.01); B01J 35/1023 (2013.01); B01J 35/1028 (2013.01); B01J 35/1038 (2013.01); B01J 35/1042 (2013.01); B01J 35/1047 (2013.01); B01J 35/1061 (2013.01); B01J 37/0203 (2013.01); B01J 37/0205 (2013.01); B01J 37/036 (2013.01); C07C 1/20 (2013.01); B01J 21/08 (2013.01); B01J 37/08 (2013.01); *B01J 37/10* (2013.01); *B01J 2523/00* (2013.01); *C07C 2521/06* (2013.01); *C07C 2521/08* (2013.01); *C07C 2523/06* (2013.01); *C07C 2523/20* (2013.01)

(58) Field of Classification Search
None
See application file for complete search history.

(56) References Cited

U.S. PATENT DOCUMENTS

| 4,240,931 A * | 12/1980 | Milberger ................ B01J 23/28 502/306 |
| 4,400,306 A * | 8/1983 | Dria ....................... B01J 23/002 502/171 |
| 4,729,980 A * | 3/1988 | Ramirez de Agudelo .................. C10G 45/08 502/221 |
| 2004/0152586 A1* | 8/2004 | Ou ......................... B01J 23/002 502/64 |
| 2006/0088469 A1* | 4/2006 | Perez-Ramirez ............................ B01D 53/8628 423/701 |
| 2016/0039970 A1* | 2/2016 | Kron ........................ C08G 8/10 423/445 R |

FOREIGN PATENT DOCUMENTS

| FR | 925617 A | | 9/1947 |
| KR | 2014050531 | * | 4/2014 |
| KR | 2014050531 A | | 4/2014 |
| WO | WO2012/015340 | * | 2/2012 |

OTHER PUBLICATIONS

Synthesis of the supported catalysts by co-impregnation and sequential impregnation methods. (Khoirina Dwi Nugrahaningtyas et al., International Conference on Advanced Materials for Better Future 2016) (doi: 10.1088/1757-899X/176/1/012024. (Year: 2017).*
International Search Report PCT/EP2016/065824 dated Aug. 24, 2016.
B. B. Corson et al: "Butadiene from Ethyl Alcohol", Industrial and Engineering Chemistry, vol. 41, No. 5, May 1949 (May 1, 1949), US, pp. 1012-1017, XP055262381, ISSN: 0019-7866.
B. B. Corson et al: "Butadiene from Ethyl Alcohol. Catalysis in the One-and Two-Stop Processes.", Industrial & Engineering Chemistry, vol. 42, No. 2, Feb. 1950 (Feb. 1, 1950), pp. 359-373, XP055051002, ISSN: 0019-7866.

* cited by examiner

*Primary Examiner* — Colin W. Slifka
*Assistant Examiner* — Colette B Nguyen
(74) *Attorney, Agent, or Firm* — Millen, White, Zelano and Branigan, P.C.

(57) ABSTRACT

The invention relates to a catalyst that comprises a mesoporous oxide matrix, with said matrix comprising at least one oxide of an element X that is selected from among silicon and titanium, taken by itself or in a mixture, with said catalyst comprising at least the tantalum element and the niobium element, with the tantalum mass representing between 0.1 to 30% by weight of the mass of the mesoporous oxide matrix, the niobium mass representing between 0.02 to 6% by weight of the mass of the mesoporous oxide matrix, the content by mass of the tantalum element being greater than or equal to the content by mass of the niobium element. The invention also relates to the use of this catalyst in a method for the production of 1,3-butadiene from a feedstock that comprises at least ethanol.

13 Claims, 1 Drawing Sheet

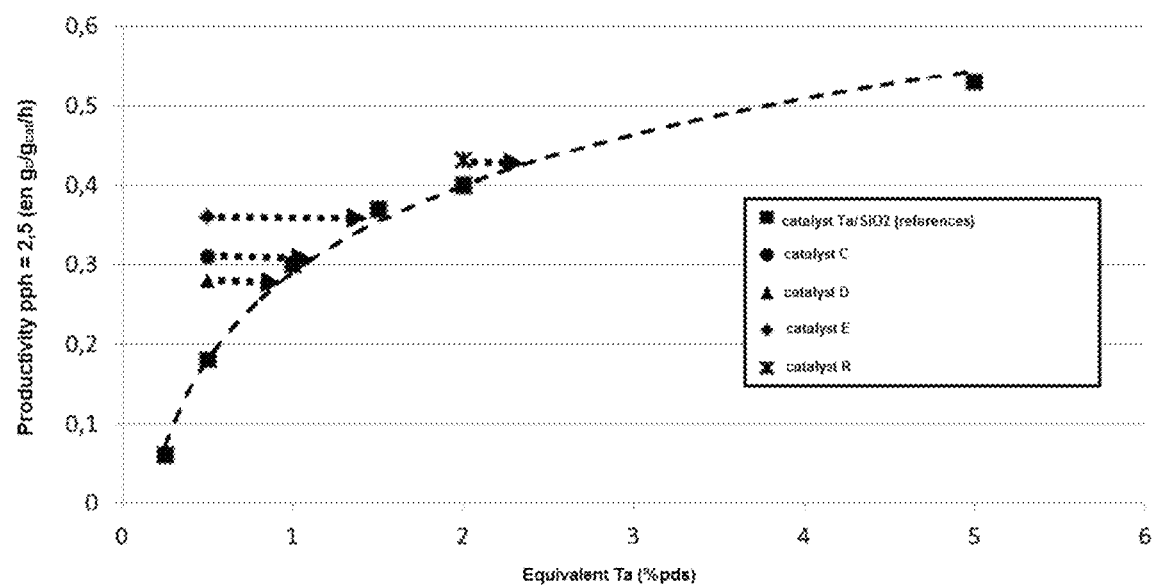

CATALYST TA-NB FOR THE PRODUCTION OF 1,3-BUTADIENE

PRIOR ART

Butadiene is widely used in the chemical industry in particular as a reagent for the production of polymers. Currently, butadiene is produced almost entirely from steam-cracking units of which it constitutes an upgradable by-product. The price fluctuation of petroleum and the ever-increasing demand for this chemical intermediate compound has made its price very volatile, which prompts a diversification of supply means. It is thus well known to one skilled in the art that 1,3-butadiene can be produced from ethanol. Two methods have been industrialized on a large scale: the "S. K. Process" and the "Carbide Process." In the "S. K. Process," the 1,3-butadiene is produced from ethanol in one step, whereas in the "Carbide Process," the 1,3-butadiene is produced in two steps: ethanol is first converted into acetaldehyde, and then an ethanol-acetaldehyde mixture is converted into 1,3-butadiene. The primary distinction between the catalysts involved in these methods is that one (SK Process) can dehydrogenate ethanol into acetaldehyde while producing butadiene from the thus formed mixture whereas the other cannot, hence the necessity for a first dehydrogenation step on a specific catalyst. The chemical elements that constitute the most effective catalysts for this method for producing butadiene are magnesium, tantalum, zirconium, hafnium, with butadiene selectivities ranging between 50 and 69%, with niobium (or colombium) being considered as a not very attractive element with selectivities that are lower than 40% (B. B. Corson, H. E. Jones, C. E. Welling, J. A. Hinckley, E. E. Stahly, *Ind. Eng. Chem.*, 1950, 42 (2), pp. 359-373).

Regardless of the method (one or two steps), the overall balance of the primary reaction is written as follows:

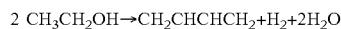

2 $CH_3CH_2OH \rightarrow CH_2CHCHCH_2 + H_2 + 2H_2O$

Numerous chemical reactions comprising a dehydrogenation reaction that makes it possible to generate acetaldehyde (I), an aldolization/crotonization reaction of acetaldehyde into crotonaldehyde (II), a Merwein-Pondorff-Verley (MPV) reaction between ethanol and crotonaldehyde (III) and finally a step for dehydration of crotylic alcohol into butadiene (IV) lie behind this overall balance.

$CH_3CH_2OH \rightleftharpoons CH_3CHO + H_2$     I:

2 $CH_3CHO \rightleftharpoons CH_3CHCH-CHO + H_2O$     II:

$CH_3CHCH-CHO + CH_3CH_2OH \rightleftharpoons CH_3CHCH-CH_2OH + CH_3CHO$     III:

$CH_3CHCH-CH_2OH \rightarrow CH_2CHCHCH_2 + H_2O$     IV:

This multiplicity of chemical reactions is at the origin of numerous by-products if the stringing-together of steps is not done in the order specified above, with in particular the presence of secondary condensation and dehydration reactions. In addition, other reactions can occur (such as isomerization, cyclization, Diels-Alder reaction, etc.), also increasing the number of by-products. In this stage, it is noted that according to the nature of the catalyst that is used for the transformation of ethanol (or of the ethanol-acetaldehyde mixture) into 1,3-butadiene, the distribution of said by-products can change greatly. Thus, the addition of an acid element will make the production of dehydration products (for example, ethylene or diethyl ether) increase whereas the addition of a basic element will promote the formation of multiple condensation products (for example, hexenes or hexadienes).

Consequently, regardless of the method (one or two steps), the selectivity of the transformation of ethanol (or of the ethanol-acetaldehyde mixture) into 1,3-butadiene is moderate. However, because of the relatively high price of the raw material, the economic study of the method shows that the effectiveness of the transformation of the feedstock constitutes a significant lever to ensure its viability. Numerous efforts have therefore been deployed to maximize this selectivity.

In particular, during the development of the method for producing butadiene from an ethanol/acetaldehyde mixture (method in two steps), the better catalyst that was found was a tantalum oxide deposited on an amorphous silica (*Ind. Eng. Chem.*, 1949, 41, pp. 1012-1017). The butadiene selectivity was 69% for an initial conversion of the feedstock of 34%. It was also shown that the use of this same catalyst in a "carbide" industrial unit led to the formation of the following majority impurities (by-products): diethyl ether (23% by weight of impurities), ethylene (11% by weight of impurities), hexenes, hexadienes (11% by weight of impurities), etc. (W. J. Toussaint, J. T. Dunn, D. R. Jackson, *Industrial and Engineering Chemistry*, 1947, 39 (2), pp. 120-125). Despite the presence of by-products, their formation is limited by the relatively low acido-basicity properties of the tantalum element. The latter also makes it possible to catalyze the reactions II, III and IV very effectively. One of its only drawbacks resides in its price.

Actually, according to the report written in 2012 by Jonathan Burla, Ross Fehnel, Philip Louie and Peter Terpeluk of the University of Pennsylvania and entitled "TWO-STEP PRODUCTION OF 1,3-BUTADIENE FROM ETHANOL," the price of silica is around $0.96/lb and that of tantalum around $162/lb. By way of indication, the current prices of niobium and zirconium are around $20/lb and $1/lb, or approximately a price ratio of one order of magnitude between niobium and tantalum and two orders of magnitude between zirconium and tantalum.

Various studies have then been carried out to optimize the effectiveness of tantalum and/or to substitute this element. For example, the application WO 2014/061917 seeks to improve the catalyst based on tantalum via the use of a silicic substrate characterized by mesopores with uniform size and morphology and distributed in a periodic way within the material (so-called mesostructured silica). The U.S. Pat. No. 2,421,361 (W. J. Toussaint, J. T. Dunn, *Carbide and Carbon Chemical Corporation*, 1947) describes a method for the preparation of butadiene that comprises the transformation of an acyclic mono-olefinic aldehyde (crotonaldehyde or acetaldehyde) and a monohydroxylated alcohol (ethanol) on a catalyst from the group of zirconium oxide, tantalum oxide, niobium oxide, and one of the combinations of these oxides with silica. However, according to the examples that are provided, the tantalum oxide that is used by itself remains the best catalyst for converting the specific ethanol/acetaldehyde mixture. According to *Ind. Eng. Chem.*, 1950, 42 (2), pp. 359-373, the best combinations for the transformation of the ethanol/acetaldehyde mixture are: Ta—Cu, Ta—Zr, Zr—Nb, Zr—Ti and Zr—Th, deposited on a silicic substrate (U.S. Pat. Nos. 2,374,433, 2,436,125, 2,438,464, 2,357,855, 2,447,181). More recently, most of the studies have sought to eliminate the tantalum from the catalytic formulation completely, in particular owing to the use of the zirconium or magnesium element:

The application WO 2014/199349 (BASF) uses a Zr, Zn, Cu combination,

The application WO 2014/180778 (Synthos) claims a Zr, Zn, La combination,

The application WO 2014/049158 (Lanxess) uses an Mg—Si mixed oxide that is doped by elements such as Ti, V, Mo, Mn, Cu, Ni, Zn or Cr, The application WO 2013/125389 (Daicel) claims the use of an Mg—Si mixed oxide that is doped by a metal that belongs to the columns 4 to 13, The application WO 2012/015340 (Unisit) uses the combination of an element in the metal state of column 11 and a metal oxide that is selected from among magnesium, titanium, zirconium, tantalum, and niobium.

SUMMARY OF THE INVENTION

The invention relates to a catalyst that comprises a mesoporous oxide matrix, with said matrix comprising at least one oxide of an element X that is selected from among silicon and titanium, taken by itself or in a mixture, with said catalyst comprising tantalum and niobium, the tantalum mass representing 0.1 to 30% of the mass of the mesoporous oxide matrix, the niobium mass representing 0.02 to 6% of the mass of the mesoporous oxide matrix, the content by mass of the tantalum element in said catalyst being greater than or equal to the content by mass of the niobium element in said catalyst.

Advantage of the Invention

One aspect of the invention is to upgrade the use of niobium as co-catalyst of tantalum during the reaction for transformation of ethanol or the ethanol-acetaldehyde mixture into 1,3-butadiene, so as to maximize the selectivity and the productivity of 1,3-butadiene via a synergetic process involving these two elements. The applicant discovered that a subtle combination of these two elements makes it possible to accelerate the formation of butadiene, by taking advantage of the affinity of tantalum for the reactions II and III and that of niobium for the reactions III and IV. The result is, surprisingly enough, a synergetic effect that can be observed by the increase in productivity in relation to the weighted mean of the productivities induced by the Ta and Nb elements that are taken separately and by the improvement in the selectivity of the reaction in relation to the weighted mean of the selectivities induced by the Ta and Nb elements that are tested separately. This invention makes possible an improvement in the selectivity and/or the productivity with iso-conversion of the feedstock.

In addition, the niobium element proves to be a particularly advantageous candidate for partially substituting tantalum and thus reducing the production costs of the catalyst. Thus, for a given butadiene production, the quantity of tantalum used is decreased. The invention therefore makes it possible to improve the costs with a catalyst that has at least the same performances with operating iso conditions but with a smaller content of tantalum than a catalyst based on tantalum alone.

Disclosure of the Invention

This invention relates to the synergetic combination of tantalum and niobium elements on the same catalyst in a method for producing butadiene from ethanol, with this method able to operate in several reaction steps (one step or two steps). This synergy manifests itself both by a rise in productivity and a rise in selectivity comparatively to the performances of catalysts based on tantalum (niobium excluded) and catalysts based on niobium (tantalum excluded) in the form of extrudates that are tested separately or by mechanical mixing.

This invention therefore makes it possible to improve in a significant way the method for producing butadiene by limiting the losses of raw materials in the form of undesirable by-products and by limiting the impact of the cost of the catalyst on the latter.

The invention therefore relates to a catalyst, and its use for the production of 1,3-butadiene from a feedstock that comprises at least ethanol, comprising at least the tantalum and niobium elements and at least one mesoporous oxide matrix.

The catalyst according to the invention comprises tantalum, with the tantalum mass representing between 0.1 and 30%, preferably between 0.3 and 10%, in a preferred way between 0.5 and 5%, and in a very preferred manner between 0.5 and 2% of the mass of the mesoporous oxide matrix.

Catalyst comprising an element A, with the mass of the element A being encompassed—or being represented—between x and y % of the mass of the mesoporous oxide matrix, is defined as said catalyst comprising between x and y parts by weight of said element A per 100 parts by weight of said mesoporous oxide matrix.

The catalyst according to the invention also comprises niobium, with the niobium mass representing between 0.02 and 6%, preferably between 0.02 and 2%, in a preferred way between 0.05 and 1%, and in a very preferred manner between 0.05 and 0.5% of the mass of the mesoporous oxide matrix.

In addition, the tantalum and niobium elements are introduced into the catalyst according to the invention in such a way that the content by mass of the tantalum element that is expressed in terms of % by weight of metal in relation to the mass of the mesoporous oxide matrix is greater than or equal to the content by mass of the niobium element that is expressed in terms of % by weight of metal in relation to the mass of the mesoporous oxide matrix, with the % by weight of metal being calculated as the ratio of the mass of metal to the mass of the mesoporous oxide matrix.

The catalyst according to the invention advantageously also comprises at least one element that is selected from the group that consists of the elements of groups 1, 2, 3, and 4 of the periodic table and mixtures thereof, preferably at least one element that is selected from among the group that consists of the elements of groups 1 and 2 of the periodic table and mixtures thereof and in an even more preferred way of at least one element that is selected from the group that consists of the Cs element of group 1 and the Ca and Ba elements of group 2 of the periodic table and mixtures thereof, with the mass of said element representing between 0.01 and 5%, preferably between 0.01 and 1%, in a preferred way between 0.01 and 0.5% of the mass of the mesoporous oxide matrix.

The addition of at least one element that is selected from the group that consists of the elements of groups 1, 2, 3 and 4 of the periodic table and mixtures thereof, preferably at least one element that is selected from among the group that consists of the elements of groups 1 and 2 of the periodic table and mixtures thereof and in an even more preferred way of at least one element that is selected from the group that consists of the Cs element of group 1 and the Ca and Ba elements of group 2 of the periodic table and mixtures thereof makes it possible to improve the selectivity of the catalyst according to the invention at the cost of a loss in productivity.

In a particular arrangement, the catalyst according to the invention advantageously also comprises at least one element that is selected from the group that consists of the elements of groups 11 and 12 of the periodic table and mixtures thereof, i.e., the periodic table of elements, in a more preferred way at least one element that is selected from the elements of group 12 of the periodic table and mixtures thereof and in an even more preferred way the Zn element, with the mass of said element representing between 0.5 and 10%, and preferably between 1 and 5% of the mass of said mesoporous oxide matrix based on silica. This arrangement is particularly advantageous in the case where the catalyst according to the invention is used in a one-step method, i.e., in a method that processes a feedstock that comprises primarily ethanol. Primarily ethanol is defined as the ratio by mass of ethanol to acetaldehyde in said feedstock, when said feedstock comprises acetaldehyde, being at least greater than 1, preferably at least greater than 5, with said feedstock also able to not comprise acetaldehyde.

The matrix of the catalyst according to the invention is mesoporous and comprises at least one oxide of an element X that is selected from among silicon, titanium and mixtures thereof. Preferably, the element X is silicon. Said oxide matrix is mesoporous, i.e., it is characterized by the presence of pores whose size varies between 2 and 50 nm according to the IUPAC classification (K. S. W. Sing, D. H. Everett, R. A. Haul, L. Moscou, J. Pierotti, J. Rouquerol, T. Siemieniewska, *Pure Appl. Chem.*, 1985, 57, 603). In addition to being mesoporous, said matrix can be mesostructured (i.e., can have mesopores of uniform size and distributed in a periodic way in said matrix) or else with hierarchized porosity (presence of micropores and/or macropores in addition to mesopores). In a very preferred way, the mesoporous oxide matrix that constitutes the catalyst according to the invention is a mesoporous amorphous silica with a non-organized porosity without micropores.

More particularly, the silicon oxides (silicas) that have a specific surface area of 100 to 1,200 $m^2/g$ and preferably at least 400 $m^2/g$, a mesopore volume of between 0.2 and 1.8 ml/g and preferably at least 0.6 ml/g, and a mesopore diameter of between 4 and 50 nm and preferably at least 6 nm will be used. It is possible to use, for example, a Davisil Grade 636 commercial silica ($S_{BET} \approx 500$ $m^2/g$, $V_p \approx 0.9$ ml/g and $\phi \approx 7$ nm). In an advantageous manner, the matrix of the catalyst according to the invention does not undergo acidic washing.

More particularly, the silicon oxides (silicas) that contain a content of alkaline metals that are expressed in terms of % by weight of metal in relation to the mass of the mesoporous matrix that is less than 1% by weight, preferably less than 0.5% by weight, and in a very preferred way less than 0.1% by weight, will be used.

The catalyst according to the invention can be prepared according to the methods that are known to one skilled in the art. The tantalum and niobium elements, just as for the possible additional element, constituting the catalyst according to the invention, can therefore be introduced by any method that is known to one skilled in the art and at any step of the preparation of the catalyst according to the invention.

The catalyst according to the invention is prepared by consecutive introduction of the niobium element and then of the tantalum element. The applicant actually observed that, in a surprising manner, the catalyst according to the invention that is prepared by introducing first the niobium element and then the tantalum element exhibited performances that are superior to the catalysts that are prepared by introducing first, or simultaneously, the tantalum element and then the niobium element, in particular in the uses according to the invention.

Thus, the tantalum and niobium elements, just as the possible additional element, constituting the catalyst according to the invention, can be introduced by deposition of precursors associated with the surface of a preformed mesoporous oxide matrix. The latter can be commercial or else custom-synthesized according to the methods that are known to one skilled in the art, in particular by using so-called "sol-gel" synthesis methods (see the definition below). For example, and in a non-exhaustive way, the so-called dry impregnation, excess impregnation, CVD (Chemical Vapor Deposition or chemical deposition in the vapor phase), and CLD (Chemical Liquid Deposition or chemical deposition in the liquid phase) methods, etc., can be employed.

Another option consists in using as a method for preparation of the catalyst according to the invention any of the synthesis methods that are known to one skilled in the art, making it possible to introduce the precursors that are associated with the tantalum and niobium elements, just as those associated with the possible additional element, directly during the synthesis of the preformed mesoporous oxide matrix that is selected. For example and in a non-exhaustive way, the synthesis methodologies that are employed can be inorganic "traditional" synthesis methods (precipitation/gelling from salts under mild temperature and pressure conditions) or "modern" metallo-organic methods (precipitation/gelling from alkoxides under mild temperature and pressure conditions), with the latter able to be referred to in a simplified way as "sol-gel" methods. It is also possible to use "sol-gel" methods that are combined with the use of specific synthesis methods such as spray-drying (also called atomization), dip-coating, etc.

According to a preferred embodiment of this invention, the methods that make it possible to ensure the best dispersion of the tantalum and niobium elements, just as the possible additional element, are selected so as to maximize the productivity and the selectivity of the catalyst according to the invention.

For a deposition of the precursors of these elements on the surface of the preformed mesoporous oxide matrix, the so-called dry impregnation method is preferred. No particular limitation exists relative to the number of times that said dry impregnation step is repeated. The various steps can be carried out using one or more solvents or mixture of solvents in which the precursors of the tantalum and niobium elements, just as the possible additional element, are soluble. These solvents can be polar/protic such as water, methanol or ethanol, polar/aprotic such as toluene or xylene, or apolar/aprotic such as hexane. The acidity of the solutions can also be adapted (addition of acid) to improve the solubility of the radicals. Likewise, each of the elements from among the tantalum and niobium elements and the possible additional element can be impregnated by itself or else co-impregnated with at least one of the other elements, with the sole limitation being the joint presence of the tantalum and niobium elements at the end of the method for preparation of the catalyst according to the invention. A preferred mode consists in carrying out a first dry impregnation of the niobium element and then, consecutively, a second dry impregnation of the tantalum element. A dry-impregnation-type step comprises, for example, the following operations:

(a) Dissolution of at least one precursor of the tantalum and niobium elements and the possible additional element in a solution volume that corresponds to the pore volume of the preformed mesoporous oxide matrix that is selected, (b) Impregnation of the solution that is obtained during the operation (a) on the surface of the preformed mesoporous oxide matrix that is selected, (c) Possible curing of the solid that is thus obtained in an atmosphere and at a temperature that are controlled in such a way as to promote the dispersion of at least said precursor that is used according to the invention over the entire surface of the preformed mesoporous oxide matrix that is selected, (d) Possible (hydro)thermal post-treatment(s) of the solid that is obtained during the operation (c) (drying and/or calcination, and/or steaming, etc.) in such a way as to obtain an intermediate solid or, ultimately, the catalyst according to the invention.

For an introduction of precursors associated with tantalum and niobium elements, just as those associated with the possible additional element, directly during the synthesis of the mesoporous oxide matrix, the methods for "sol-gel" synthesis by precipitation and atomization are preferred. In an even more preferred way, the method for "sol-gel" synthesis by precipitation is favored.

In the particular case of a sol-gel synthesis by precipitation leading to obtaining a catalyst that is characterized by a matrix based on mesoporous oxide with a non-organized porosity, the method for preparation of said catalyst according to the invention comprises, for example, the following operations:

a) Dissolution of at least one precursor of at least the element X that constitutes the mesoporous oxide matrix that is selected in aqueous, organic or aquo-organic medium, optionally in the presence of an acid or a base, in such a way as to form an optionally colloidal solution, b) Addition to the solution that is obtained during the operation (a) of at least one precursor of the tantalum and niobium elements and the possible additional element, in the pure state or dissolved in a suitable medium that is compatible with said solution that is obtained from operation (a). Operation (b) can be repeated as many times as necessary, in particular during the addition of the various tantalum and niobium elements, which occurs at different times, and the possible additional element, c) Precipitation of the mesoporous oxide matrix that is selected and that contains the tantalum and niobium elements and the possible additional element by the addition of an acid, a base, or by application of a specific reaction temperature, d) Filtration followed by possible washing cycles or evaporation of the suspension that is obtained during operation (c), e) (Hydro)thermal post-treatment(s) of the solid that is obtained in step (d) (drying and calcination, or steaming, etc.) in such a way as to obtain the catalyst that is used according to the invention.

The precursor(s) of at least said element X that is selected from among silicon, titanium and mixtures thereof and that constitutes the mesoporous oxide matrix, used during operation (a), can be any compound that comprises the element X and that can release this element in solution in reactive form. Thus, the precursor(s) of at least said element X is (are) advantageously an inorganic salt of said element X of formula $XZ_n$, (n=3 or 4), with Z being a halogen, the group $NO_3$, or a perchlorate. The precursor(s) of at least said element X that is/are being considered can also be (an) alkoxide precursor(s) of formula $X(OR)_n$ where R=ethyl, isopropyl, n-butyl, s-butyl, t-butyl, etc., or a chelated precursor such as $X(C_5H_8O_2)_n$ with n=3 or 4. The precursor(s) of at least said element X that is/are being considered can also be (an) oxide(s) or (a) hydroxide(s) of said element X. In the preferred case where X is silicon, the silicic precursor is obtained from any silica source and advantageously from a sodium silicate precursor of formula $Na_2SiO_3$, a chlorinated precursor of formula $SiCl_4$, an alkoxide precursor of formula $Si(OR)_4$ where R=H, methyl, ethyl or a chloro-alkoxide precursor of formula $Si(OR)_{4-a}Cl_a$ where R=H, methyl, ethyl, with a being encompassed between 0 and 4. The silicic precursor can also advantageously be an alkoxide precursor of formula $Si(OR)_{4-a}R'_a$, where R=H, methyl, ethyl and R' is an alkyl chain or an alkyl chain that is functionalized, for example, by a thiol, amino, β diketone, or sulfonic acid group, with a being encompassed between 0 and 4. A preferred silicic precursor is tetraethyl orthosilicate (TEOS).

Regardless of the method for incorporating the tantalum and niobium elements and the possible additional element, the precursors of the latter are any compound that comprises at least the tantalum or niobium element or the possible additional element and that can release this element in solution in reactive form. Thus, the precursors of at least the tantalum or niobium element or the possible additional element are advantageously inorganic salts and alkoxide precursors. The inorganic salts are selected from the group that consists of the halides, the nitrates, the sulfates, the phosphates, the hydroxides, the carbonates, the carboxylates, the alcoholates, and combinations of two or more of the former, more preferably selected from the group that consists of the chlorides, the nitrates, the carboxylates, the alcoholates, and combinations of two or more of the former. The alkoxide precursors have for a formula, for example, $M(OR)_n$, where M=Nb, Ta, etc., and R=ethyl, isopropyl, n-butyl, s-butyl, t-butyl, etc., or a chelated precursor such as $X(C_5H_8O_2)_n$, with n=3 or 4. For example, the preferred precursors of tantalum are tantalum pentachloride and tantalum pentaethanoate, which can be used with most organic solvents. The preferred precursors of niobium are ammonium oxalate and niobium oxalate or niobium pentaethoxide.

The catalyst according to the invention can be shaped in the form of balls, pellets, granules, or extrudates (cylinders that may or may not be hollow, multilobed cylinders with 2, 3, 4 or 5 lobes, for example, twisted cylinders), or rings, etc., with these shaping operations being carried out by the conventional techniques that are known by one skilled in the art. Preferably, said catalyst that is used according to the invention is obtained in the form of extrudates of a size of between 1 and 10 mm. However, it is not impossible that said materials that are obtained will then be, for example, introduced into a piece of equipment that makes it possible to round their surfaces, such as a bezel or any other piece of equipment that makes it possible to make them spherical in shape.

During the shaping operation, the catalyst according to the invention can optionally be mixed with at least one porous oxide material that has the role of binder so as to generate the physical properties of the catalyst that are suited to the method (mechanical strength, resistance to attrition, etc.).

Said porous oxide material is preferably a porous oxide material that is selected from the group that is formed by silica, magnesia, clays, titanium oxide, lanthanum oxide, cerium oxide, boron phosphates, and a mixture of at least two of the oxides cited above. It is also possible to use titanates, for example the titanates of zinc, nickel, cobalt. It is also possible to use simple, synthetic or natural clays of the 2:1 dioctahedral phyllosilicate type or the 3:1 trioctahedral phyllosilicate type such as kaolinite, antigorite, chrysotile, montmorillonnite, beidellite, vermiculite, talc, hectorite, saponite, laponite. The clays can optionally be delaminated. The various mixtures that use at least two of the compounds cited above are also suitable for ensuring the binder role.

In a very preferred way, the binder that is used has a silicic nature. For example and in a non-exhaustive way, said silicic binder can be in the form of colloidal solutions or powders.

Preferably, said catalyst comprises—and preferably consists of—5 to 60% by weight, and in a preferred manner between 10 and 30% by weight, of silicic binder, with the percentages by weight being expressed in relation to the total mass of said catalyst.

Optionally, at least one organic adjuvant is also mixed during said shaping step. The presence of said organic adjuvant facilitates the shaping by extrusion. Said organic adjuvant can advantageously be selected from among methyl cellulose, hydroxypropyl methylcellulose, hydroxyethyl cellulose, carboxymethylcellulose, and polyvinyl alcohol. The proportion of said organic adjuvant is advantageously between 0 and 20% by weight, preferably between 0 and 10% by weight, and in a preferred manner between 0 and 7% by weight, in relation to the total mass of said shaped material.

Based on the method for preparation of the catalyst according to the invention that is selected, it is also possible to carry out said shaping step directly on the mesoporous oxide matrix that constitutes the catalyst according to the invention. In this case, the introduction of the tantalum and niobium elements and the possible additional element is carried out as described above via a deposition of precursors of these elements on the surface of the preformed and shaped mesoporous oxide matrix.

Regardless of the method for incorporating tantalum and niobium elements and the possible additional element, constituting the catalyst according to the invention, and regardless of the shaping steps that are selected, a (hydro)thermal post-treatment step (drying and/or calcination, and/or steaming, etc.) is applied in such a way as to obtain the catalyst according to the invention. Preferably, the applied post-treatment is a calcination in air in an oven in a temperature range of 300 to 800° C., in a preferred way from T=450° C. to T=700° C. and in an even more preferred way from T=540° C. to T=700° C., for a period of less than 24 hours and preferably less than 12 hours.

The nitrogen volumetric analysis corresponding to the physical adsorption of nitrogen molecules in the porosity of the catalyst according to the invention via a gradual increase in pressure at constant temperature provides information on the particular textural characteristics (pore diameter, pore volume, specific surface area) of the material that is used according to the invention. In particular, it makes it possible to access the specific surface area and the mesopore distribution of the catalyst. Specific surface area is defined as the BET specific surface area ($S_{BET}$ in $m^2/g$) that is determined by nitrogen adsorption in accordance with the ASTM D 3663-78 standard established from the BRUNAUER-EMMETT-TELLER method described in the periodical "The Journal of American Society," 1938, 60, 309. The pore distribution that is representative of a mesopore population centered in a range of from 2 to 50 nm (IUPAC classification) is determined by the Barrett-Joyner-Halenda (BJH) model. The nitrogen adsorption-desorption isotherm according to the BJH model that is thus obtained is described in the periodical "The Journal of American Society," 1951, 73, 373, written by E. P. Barrett, L. G. Joyner and P. P. Halenda. In the following disclosure, the diameter of mesopores f of the oxide-based matrix corresponds to the value of the maximum diameter that is read on the pore size distribution curve obtained from the adsorption branch of the nitrogen isotherm. In addition, the form of the nitrogen adsorption isotherm and the hysteresis loop can provide information on the nature of the mesoporosity and the presence of the possible microporosity of the catalyst according to the invention. The quantitative analysis of the microporosity of the inorganic material that is obtained according to the invention is carried out from methods "t" (Lippens-De Boer method, 1965) or "$\alpha_s$" (method proposed by Sing) that correspond to transforms of the initial adsorption isotherm as described in the work "Adsorption by Powders and Porous Solids. Principles, Methodology and Applications" written by F. Rouquerol, J. Rouquerol and K. Sing, Academic Press, 1999. These methods make it possible to access in particular the value of the characteristic micropore volume of the microporosity of the catalyst according to the invention.

In the following disclosure of the invention, the pore distribution that is measured by mercury porosimetry is determined by mercury porosimeter intrusion according to the ASTM D4284-83 standard at a maximum pressure of 4,000 bar (400 MPa), using a surface tension of 484 dyne/cm and a contact angle of 140°. The wetting angle was assumed to be equal to 140° by following the recommendations of the work "Techniques de l'ingénieur, traité analyse et caracterisation [Engineering Techniques, Analytical Treatise and Characterization], pp. 1050-5, written by Jean Charpin and Bernard Rasneur."

The value beyond which the mercury fills all of the intergranular gaps is set at 0.2 MPa, and it is considered that beyond this, the mercury penetrates into the pores of the solid.

So as to obtain a better precision, the value of the total pore volume corresponds to the value of the total pore volume that is measured by mercury porosimeter intrusion that is measured on the sample minus the value of the total pore volume that is measured by mercury porosimeter intrusion measured on the same sample for a pressure that corresponds to 30 psi (approximately 0.2 MPa).

The macropore volume of the catalyst is defined as being the cumulative volume of mercury that is introduced at a pressure of between 0.2 MPa and 30 MPa, corresponding to the volume that is contained in the pores with an apparent diameter of greater than 50 nm.

The mesopore volume of the catalyst is defined as being the cumulative volume of mercury that is introduced at a pressure of between 30 MPa and 400 MPa, corresponding to the volume that is contained in the pores with an apparent diameter of between 2 and 50 nm.

The use of a catalyst that comprises at least the tantalum and niobium elements and at least one mesoporous oxide matrix for the conversion of ethanol or an ethanol/acetaldehyde mixture into butadiene manifests itself in significant performance advantages in terms of productivity and selectivity. The representative conditions for this reaction (conditions for which a better productivity and a better selectivity are observed) are a temperature of between 300 and 400°

C., preferably between 320° C. and 380° C., a pressure of between 0.15 and 0.5 MPa, preferably between 0.15 and 0.3 MPa, a volumetric flow rate of between 0.5 and 5 h$^{-1}$, preferably between 1 and 4 h$^{-1}$, and, in the case of the "two-step" method where the feedstock comprises ethanol and acetaldehyde, a ratio by mass of ethanol/acetaldehyde of between 1 and 30, in a preferred manner between 2 and 10. The volumetric flow rate is defined as the ratio between the mass flow rate of the feedstock and the catalyst mass.

BRIEF DESCRIPTION OF THE DRAWINGS

FIG. 1 represents a curve showing the relationship between tantalum content of the catalyst and butadiene productivity The invention is illustrated by means of the following examples.

EXAMPLES

Example 1: Preparation of the Catalyst a Based on 0.5% Ta/SiO$_2$$^\alpha$ (0.5% by Weight of Ta in Relation to the Silica Mass) that is Obtained by Dry Impregnation of the Tantalum Precursor that is Attached to the Surface of the Davisil 636 Commercial Silica (α) (for Comparison Purposes)

0.67 g of tantalum ethoxide (Ta(OCH$_2$CH$_3$)$_5$) is diluted in 96 ml of ethanol. This solution is quickly added drop by drop and mixed with 60 g of the Davisil 636 silica (SBET≈500 m$^2$/g, Vp≈0.9 ml/g and φ≈7 nm, granulometry: 200-500 microns) until wettability of the surface of the latter (dry impregnation) is observed. The solid is then placed in an ethanol-saturated atmosphere for 3 hours, dried at 100° C. for 24 hours. The catalyst A is obtained by calcination of the solid that is dried in air at 550° C. for 4 hours.

Example 2: Preparation of the Catalysts B, B' and B" Based on 0.5% Nb/SiO$_2$$^\alpha$, 0.25% Nb/SiO$_2$$^\alpha$ and 1% Nb/SiO$_2$$^\alpha$ (0.5%, 0.25% and 1% by Weight of Nb in Relation to the Silica Mass) that is Obtained by Dry Impregnation of the Niobium Precursor that is Attached to the Surface of the Davisil 636 Commercial Silica (α) (for Comparison Purposes)

1.06 g of niobium oxalate and pentahydrated ammonium oxolate is diluted in 80 ml of water. This solution is quickly added drop by drop and mixed with 50 g of the Davisil 636 silica (SBET≈500 m$^2$/g, Vp≈0.9 ml/g and φ≈7 nm, granulometry: 200-500 microns) until wettability of the surface of the latter (dry impregnation) is observed. The solid is then placed in a water-saturated atmosphere for 3 hours, dried at 100° C. for 24 hours. The catalyst B is obtained by calcination of the solid that is dried in air at 550° C. for 4 hours.

The catalyst B' is prepared in a similar way with a precursor content that is 2× smaller (0.53 g of niobium oxalate and pentahydrated ammonium oxalate).

The catalyst B" is prepared in a similar way with a precursor content that is 2× larger (2.12 g of niobium oxalate and pentahydrated ammonium oxalate).

Example 3: Preparation of the Catalyst C Based on 0.5% Nb/0.5% Ta/SiO$_2$$^\alpha$ (0.5% by Weight of Nb and Ta in Relation to the Silica Mass) that is Obtained by Successive Dry Impregnations of the Niobium and Tantalum Precursors Attached to the Surface of the Davisil 636 Commercial Silica (α) with Intermediate Calcination (for Comparison Purposes)

1.05 g of niobium oxalate and pentahydrated ammonium oxalate is diluted in 80 ml of water. This solution is quickly added drop by drop and mixed with 50 g of the catalyst A until wettability of the surface of the latter (dry impregnation) is observed. The solid is then placed in a water-saturated atmosphere for 3 hours, dried at 100° C. for 24 hours. The catalyst C is obtained by calcination of the solid that is dried in air at 550° C. for 4 hours.

Example 4: Preparation of the Catalyst D Based on 0.5% Nb/0.5% Ta/SiO$_2$$^\alpha$ (0.5% by Weight of Nb and Ta in Relation to the Silica Mass) that is Obtained by Successive Dry Impregnations of the Niobium and Tantalum Precursors that are Attached to the Surface of the Davisil 636 Commercial Silica (α) with Intermediate Drying (for Comparison Purposes)

0.67 g of tantalum ethoxide (Ta(OCH$_2$CH$_3$)$_5$) is diluted in 96 ml of ethanol. This solution is quickly added drop by drop and mixed with 60 g of the Davisil 636 silica (SBET≈500 m$^2$/g, Vp≈0.9 ml/g and φ≈7 nm, granulometry: 200-500 microns) until wettability of the surface of the latter (dry impregnation) is observed. The solid is then placed in an ethanol-saturated atmosphere for 3 hours, dried at 100° C. for 24 hours. 1.27 g of niobium oxalate and pentahydrated ammonium oxalate is diluted in 96 ml of water. This solution is quickly added drop by drop and mixed with the dried solid until wettability of the surface of the latter (dry impregnation) is observed. The latter is then placed in a water-saturated atmosphere for 3 hours, dried at 100° C. for 24 hours. The catalyst D is obtained by calcination of the solid that is dried in air at 550° C. for 4 hours.

Example 5: Preparation of the Catalyst E Based on 0.5% Ta/0.5% Nb/SiO$_2$$^\alpha$ (0.5% by Weight of Nb and Ta in Relation to the Silica Mass) Obtained by Successive Dry Impregnations of the Niobium and Tantalum Precursors that are Attached to the Surface of the Davisil 636 Commercial Silica (α) with Intermediate Calcination (According to the Invention)

0.33 g of tantalum ethoxide (Ta(OCH$_2$CH$_3$)$_5$) is diluted in 48 ml of ethanol. This solution is quickly added drop by drop and mixed with 30 g of the catalyst B until wettability of the surface of the latter (dry impregnation) is observed. The solid is then placed in an ethanol-saturated atmosphere for 3 hours, dried at 100° C. for 24 hours. The catalyst E is obtained by calcination of the solid that is dried in air at 550° C. for 4 hours.

Example 6: Preparation of the Catalyst F Based on 0.25% Nb/0.5% Ta/SiO$_2$$^\alpha$ (0.25% By Weight of Nb and 0.5% by Weight of Ta in Relation to the Silica Mass) that is Obtained by Dry Impregnation of the Niobium and Tantalum Precursors Attached to the Surface of the Davisil 636 Commercial Slica (α) (for Comparison Purposes)

0.53 g of niobium oxalate and pentahydrated ammonium oxalate is diluted in 80 ml of water. This solution is quickly added drop by drop and mixed with 50 g of the catalyst A until wettability of the surface of the latter (dry impregnation) is observed. The solid is then placed in a water-saturated atmosphere for 3 hours, dried at 100° C. for 24 hours. The catalyst F is obtained by calcination of the solid that is dried in air at 550° C. for 4 hours.

Example 7: Preparation of the Catalysts F' and F'''
Based on 1% Nb/0.5% Ta/SiO$_2$$^\alpha$ (1% by Weight of
Nb and 0.5% by Weight of Ta in Relation to the
Silica Mass) that is Obtained by Dry Impregnation
of the Niobium and Tantalum Precursors that are
Attached to the Surface of the Davisil 636
Commercial Silica ($\alpha$) (Outside of the Invention)

2.12 g of niobium oxalate and pentahydrated ammonium oxalate is diluted in 80 ml of water. This solution is quickly added drop by drop and mixed with 50 g of the catalyst A until wettability of the surface of the latter (dry impregnation) is observed. The solid is then placed in a water-saturated atmosphere for 3 hours, dried at 100° C. for 24 hours. The catalyst F' is obtained by calcination of the solid that is dried in air at 550° C. for 4 hours.

2.54 g of niobium oxalate and pentahydrated ammonium oxalate is diluted in 80 ml of water. This solution is quickly added drop by drop and mixed with 60 g of the Davisil 636 silica (SBET≈500 m$^2$/g, Vp≈0.9 ml/g and $\phi$=7 nm, granulometry: 200-500 microns) until wettability of the surface of the latter (dry impregnation) is observed. The solid that is obtained is then placed in a water-saturated atmosphere for 3 hours, dried at 100° C. for 24 hours.

0.67 g of tantalum ethoxide (Ta(OCH$_2$CH$_3$)$_5$) is diluted in 96 ml of ethanol. This solution is quickly added drop by drop and mixed with the solid that is obtained until wettability of the surface of the latter (dry impregnation) is observed. The solid is then placed in an ethanol-saturated atmosphere for 3 hours, dried at 100° C. for 24 hours. The catalyst F''' is obtained by calcination of the solid that is dried in air at 550° C. for 4 hours.

Example 8: Preparation of the Catalyst G Based on
1% Ta/SiO$_2$$^\alpha$ (1% by Weight of Ta in Relation to
the Silica Mass) that is Obtained by Dry
Impregnation of the Tantalum Precursor that is
Attached to the Surface of the Davisil 636
Commercial Silica ($\alpha$) (for Comparison Purposes)

1.34 g of tantalum ethoxide (Ta(OCH$_2$CH$_3$)$_5$) is diluted in 96 ml of ethanol. This solution is quickly added drop by drop and mixed with 60 g of the Davisil 636 silica (SBET≈500 m$^2$/g, Vp≈0.9 ml/g and $\phi$≈7 nm, granulometry: 200-500 microns) until wettability of the surface of the latter (dry impregnation) is observed. The solid is then placed in an ethanol-saturated atmosphere for 3 hours, dried at 100° C. for 24 hours. The catalyst G is obtained by calcination of the solid that is dried in air at 550° C. for 4 hours.

Example 9: Preparation of the Catalyst H 0.5%
Ta/SiO$_2$$^\alpha$ (0.5% by Weight of Ta in Relation to the
Silica Mass) that is Obtained by Dry Impregnation
of the Tantalum Precursor that is Attached to the
Surface of a Synthesized Silica ($\beta$) Along the
Metallo-Organic Modern Sol-Gel Path (for
Comparison Purposes)

Preparation of the Silica:
12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 50 ml of a 14% (by volume) ammonia solution is then added. The system is disturbed, and a gel forms. 19 ml of ethanol is then added to make possible additional stirring for 3 hours. The final gel is filtered, washed with ethanol and then dried at 100° C. for 24 hours. The silica powder that is obtained is then calcined in air at 550° C. for 4 hours.

Preparation of the Catalyst:
0.11 g of tantalum ethoxide (Ta(OCH$_2$CH$_3$)$_5$) is dissolved in 31.7 ml of ethanol. This solution is added drop by drop and mixed with 10 g of silica until wettability of the surface of the latter (dry impregnation) is observed. The solid is then placed in an ethanol-saturated atmosphere for 3 hours, dried at 100° C. for 24 hours. The catalyst H is obtained by calcination of the solid that is dried in air at 550° C. for 4 hours.

Example 10: Preparation of the Catalyst I 0.5%
Nb/SiO$_2$$^\beta$ (0.5% by Weight of Nb in Relation to
the Silica Mass) that is Obtained by Dry
Impregnation of the Niobium Precursor that is
Attached to the Surface of a Synthesized Silica ($\beta$)
Along the Metallo-Organic Modern Sol-Gel Path
(for Comparison Purposes)

Preparation of the Silica:
12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 50 ml of a 14% (by volume) ammonia solution is then added. The system is disturbed, and a gel forms. 19 ml of ethanol is then added to make possible an additional stirring for 3 hours. The final gel is filtered, washed with ethanol, and then dried at 100° C. for 24 hours. The silica powder that is obtained is then calcined in air at 550° C. for 4 hours.

Preparation of the Catalyst:
0.17 g of niobium oxalate and ammonium oxalate is dissolved in 18 ml of water. This solution is added drop by drop and mixed with 10 g of silica until wettability of the surface of the latter (dry impregnation) is observed. The solid is then placed in a water-saturated atmosphere for 3 hours, dried at 100° C. for 24 hours. The catalyst I is obtained by calcination of the solid that is dried in air at 550° C. for 4 hours.

Example 11: Preparation of the Catalyst J 0.5%
Nb/0.5% Ta/SiO$_2$$^\beta$ (0.5% by Weight of Nb and
0.5% by Weight of Ta in Relation to the Silica
Mass) that is Obtained by Dry Impregnation of the
Niobium and Tantalum Precursors that are Attached
to the Surface of a Synthesized Silica ($\beta$) Along the
Metallo-Organic Modern Sol-Gel Path (According
to the Invention)

Preparation of the Silica:
12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 50 ml of a 14% (by volume) ammonia solution is then added. The system is disturbed, and a gel forms. 19 ml of ethanol is then added to make possible additional stirring for 3 hours. The final gel is filtered, washed with ethanol, and then dried at 100° C. for 24 hours. The silica powder that is obtained is then calcined in air at 550° C. for 4 hours.

Preparation of the Catalyst:
0.17 g of niobium oxalate and ammonium oxalate is dissolved in 18 ml of water. This solution is added drop by drop and mixed with 10 g of silica until wettability of the surface of the latter (dry impregnation) is observed. The solid is then placed in a water-saturated atmosphere for 3 hours, dried at 100° C. for 24 hours. 0.11 g of tantalum ethoxide (Ta(OCH$_2$CH$_3$)$_5$) is dissolved in 31.7 ml of ethanol. This solution is added drop by drop and mixed with 10 g of the solid Nb—SiO$_2$ until wettability of the surface of the latter (dry impregnation) is observed. The solid is then placed in an ethanol-saturated atmosphere for 3 hours, dried at 100° C. for 24 hours. The catalyst J is obtained by calcination of the solid that is dried in air at 550° C. for 4 hours.

Preparation of the Catalyst J' 0.5% Nb/0.5% Ta/SiO$_2$$^β$ (0.5% by weight of Nb and 0.5% by Weight of Ta in Relation to the Silica Mass) that is Obtained by Dry Impregnation of the Niobium and Tantalum Precursors that are Attached to the Surface of a Synthesized Silica (β) Along the Metallo-Organic Modern Sol-Gel Path on which 1,000 ppm of Sodium was Deposited (According to the Invention)

Preparation of the Silica:

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 50 ml of a 14% (by volume) ammonia solution is then added. The system is disturbed, and a gel forms. 19 ml of ethanol is then added to make possible additional stirring for 3 hours. The final gel is filtered, washed with ethanol, and then dried at 100° C. for 24 hours. The silica powder that is obtained is then calcined in air at 550° C. for 4 hours.

Preparation of the Sodium-Doped Silica:

37 mg of sodium nitrate is dissolved in 18 ml of water. This solution is added drop by drop and mixed with 10 g of silica until wettability of the surface of the latter (dry impregnation) is observed. The solid is then placed in a water-saturated atmosphere for 3 hours, dried at 100° C. for 24 hours, and then calcined in air at 550° C. for 4 hours.

Preparation of the Catalyst:

0.17 g of niobium oxalate and ammonium oxalate is dissolved in 18 ml of water. This solution is added drop by drop and mixed with 10 g of silica until wettability of the surface of the latter (dry impregnation) is observed. The solid is then placed in a water-saturated atmosphere for 3 hours, dried at 100° C. for 24 hours. 0.11 g of tantalum ethoxide (Ta(OCH$_2$CH$_3$)$_5$) is dissolved in 31.7 ml of ethanol. This solution is added drop by drop and mixed with 10 g of the Nb—SiO$_2$ solid until wettability of the surface of the latter (dry impregnation) is observed. The solid is then placed in an ethanol-saturated atmosphere for 3 hours, dried at 100° C. for 24 hours. The catalyst J is obtained by calcination of the solid that is dried in air at 550° C. for 4 hours.

Example 12: Preparation of the Catalyst K Based on 2% Ta/SiO$_2$$^γ$ (2% by Weight of Ta in Relation to the Silica Mass) that is Obtained by Dry Impregnation of the Tantalum Precursor that is Attached to the Surface of the Evonik Aerolyst 3041 Commercial Silica (γ) (for Comparison Purposes)

1.35 g of tantalum ethoxide (Ta(OCH$_2$CH$_3$)$_5$) is diluted in 28 ml of ethanol. This solution is quickly added drop by drop and mixed with 30 g of Evonik extrudates (SBET≈160 m$^2$/g, Vp≈0.9 ml/g and φ≈, 25 nm) until wettability of the surface of the latter (dry impregnation) is observed. The solid is then placed in an ethanol-saturated atmosphere for 3 hours, dried at 100° C. for 24 hours. The catalyst K is obtained by calcination of the solid that is dried in air at 550° C. for 4 hours.

Example 13: Preparation of the Catalyst L Based on 0.5% Nb/SiO$_2$$^γ$ (0.5% by Weight of Nb in Relation to the Silica Mass) that is Obtained by Dry Impregnation of the Niobium Precursor that is Attached to the Surface of the Evonik Aerolyst 3041 Commercial Silica (γ) (for Comparison Purposes)

0.63 g of niobium oxalate and pentahydrated ammonium oxalate is diluted in 28 ml of water. This solution is quickly added drop by drop and mixed with 30 g of Evonik extrudates (SBET≈160 m$^2$/g, Vp≈0.9 ml/g and φ≈25 nm) until wettability of the surface of the latter (dry impregnation) is observed. The solid is then placed in a water-saturated atmosphere for 3 hours, dried at 100° C. for 24 hours. The catalyst L is obtained by calcination of the solid that is dried in air at 550° C. for 4 hours.

Example 14: Preparation of the Catalyst M Based on 0.5% Nb/2% Ta/SiO$_2$$^γ$ (0.5% by Weight of Nb and 2% by Weight of Ta in Relation to the Silica Mass) that is Obtained by Dry Impregnation of the Niobium and Tantalum Precursors that are Attached to the Surface of the Evonik Aerolyst 3041 Commercial Silica (γ) (for Comparison Purposes)

0.63 g of niobium oxalate and pentahydrated ammonium oxalate is diluted in 28 ml of water. This solution is quickly added drop by drop and mixed with 30 g of catalyst K until wettability of the surface of the latter (dry impregnation) is observed. The solid is then placed in a water-saturated atmosphere for 3 hours, dried at 100° C. for 24 hours. The catalyst M is obtained by calcination of the solid that is dried in air at 550° C. for 4 hours.

Example 15: Preparation of the Catalysts N, N' and N" Based on 0.5% Zr/SiO$_2$$^α$, 0.25% Zr/SiO$_2$$^α$ and 0.05% Zr/SiO$_2$$^α$ (0.5%, 0.25% and 0.05% by Weight of Nb in Relation to the Silica Mass) that is Obtained by Dry Impregnation of the Zirconium Precursor that is Attached to the Surface of the Davisil 636 Commercial Silica (α) (for Comparison Purposes)

0.88 g of octahydrated zirconyl chloride is diluted in 80 ml of water. This solution is quickly added drop by drop and mixed with 50 g of the Davisil 636 silica (SBET≈500 m$^2$/g, Vp≈0.9 ml/g and φ≈7 nm, granulometry: 200-500 microns) until wettability of the surface of the latter (dry impregnation) is observed. The solid is then placed in a water-saturated atmosphere for 3 hours, dried at 100° C. for 24 hours. The catalyst N is obtained by calcination of the solid that is dried in air at 550° C. for 4 hours.

The catalyst N' is prepared in a similar way with a precursor content that is 2× smaller (0.44 g of octahydrated zirconyl chloride).

The catalyst N" is prepared in a similar way with a precursor content that is 10× smaller (0.04 g of octahydrated zirconyl chloride).

Example 16: Preparation of the Catalyst O Based on 0.5% Zr/0.5% Ta/SiO$_2^\alpha$ (0.5% by Weight of Zr and Ta in Relation to the Silica Mass) that is Obtained by Successive Dry Impregnations of the Zirconium and Tantalum Precursors that are Attached to the Surface of the Davisil 636 Commercial Silica ($\alpha$) with Intermediate Calcination (for Comparison Purposes)

0.18 g of octahydrated zirconyl chloride is diluted in 15 ml of water. This solution is quickly added drop by drop and mixed with 10 g of the catalyst A until wettability of the surface of the latter (dry impregnation) is observed. The solid is then placed in a water-saturated atmosphere for 3 hours, dried at 100° C. for 24 hours. The catalyst 0 is obtained by calcination of the solid that is dried in air at 550° C. for 4 hours.

Example 17: Preparation of the Catalysts P and P' Based on 1% Nb/0.5% Zr/SiO$_2^\alpha$ and 1% Nb/0.25% Zr/SiO$_2^\alpha$ (0.5% or 0.25% by Weight of Zr and 1% by Weight of Nb in Relation to the Silica Mass) that is Obtained by Successive Dry Impregnations of the Niobium and Zirconium Precursors that are Attached to the Surface of the Davisil 636 Commercial Silica ($\alpha$) with Intermediate Calcination (for Comparison Purposes)

0.42 g of niobium oxalate and pentahydrated ammonium oxalate is diluted in 15 ml of water. This solution is quickly added drop by drop and mixed with 10 g of the catalyst N until wettability of the surface of the latter (dry impregnation) is observed. The solid is then placed in a water-saturated atmosphere for 3 hours, dried at 100° C. for 24 hours. The catalyst P is obtained by calcination of the solid that is dried in air at 550° C. for 4 hours.

The same operation is repeated on the catalyst N' to obtain the catalyst P'.

Example 18: Preparation of the Catalyst R Based on 0.5% Nb/2% Ta/SiO$_2^\alpha$ (0.5% and 2% by Weight of Nb and Ta in Relation to the Silica Mass) that is Obtained by Successive Dry Impregnations of the Niobium and Tantalum Precursors that are Attached to the Surface of the Davisil 636 Commercial Silica ($\alpha$) with Intermediate Drying (for Comparison Purposes)

2.68 g of tantalum ethoxide (Ta(OCH$_2$CH$_3$)$_5$) is diluted in 96 ml of ethanol. This solution is quickly added drop by drop and mixed with 60 g of the Davisil 636 silica (SBET$\approx$500 m$^2$/g, Vp$\approx$0.9 ml/g and $\phi\approx$7 nm, granulometry: 200-500 microns) until wettability of the surface of the latter (dry impregnation) is observed. The solid is then placed in an ethanol-saturated atmosphere for 3 hours, dried at 100° C. for 24 hours. 1.27 g of niobium oxalate and pentahydrated ammonium oxalate is then diluted in 96 ml of water. This solution is quickly added drop by drop and mixed with the dried solid until wettability of the surface of the latter (dry impregnation) is observed. The latter is then placed in a water-saturated atmosphere for 3 hours, dried at 100° C. for 24 hours. The catalyst R is obtained by calcination of the solid that is dried in air at 550° C. for 4 hours.

Example 19: Preparation of the Catalyst S Based on 0.75% Ta/SiO$_2^\beta$ (0.75% by Weight of Ta in Relation to the Silica Mass) that is Obtained Via the Metallo-Organic Modern Sol-Gel Path (for Comparison Purposes)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 0.25 g of tantalum ethoxide (Ta(OCH$_2$CH$_3$)$_5$) is then added drop by drop under inert conditions to the preceding mixture. 50 ml of a 14% (by volume) ammonia solution is then added. The system is disturbed, and a gel forms. 19 ml of ethanol is then added to make possible additional stirring for 3 hours. The final gel is filtered, washed with ethanol, and then dried at 100° C. for 24 hours. The catalyst S is obtained by calcination of the solid that is dried in air at 550° C. for 4 hours.

Example 20: Preparation of the Catalyst T Based on 0.25% Nb/0.5% Ta/SiO$_2^\beta$ (0.25% by Weight of Nb and 0.5% by Weight of Ta in Relation to the Silica Mass) that is Obtained by Synthesis of the Nb/SiO$_2$ Solid Via the Metallo-Organic Modern Sol-Gel Path and Dry Impregnation of the Latter By the Associated Tantalum Precursor (According to the Invention)

Preparation of the Nb—SiO$_2$ Solid:

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 0.13 g of niobium ethoxide (Nb(OCH$_2$CH$_3$)$_5$) is then added drop by drop under inert conditions to the preceding mixture. 50 ml of a 14% (by volume) ammonia solution is then added. The system is disturbed, and a gel forms. 19 ml of ethanol is then added to make possible additional stirring for 3 hours. The final gel is filtered, washed with ethanol, and then dried at 100° C. for 24 hours. The Nb—SiO$_2$ powder that is obtained is then calcined in air at 550° C. for 4 hours.

Preparation of the Catalyst:

0.11 g of tantalum ethoxide (Ta(OCH$_2$CH$_3$)$_5$) is dissolved in 31.7 ml of ethanol. This solution is added drop by drop and mixed with 10 g of the Nb—SiO$_2$ solid until wettability of the surface of the latter (dry impregnation) is observed. The solid is then placed in an ethanol-saturated atmosphere for 3 hours, dried at 100° C. for 24 hours. The catalyst T is obtained by calcination of the solid that is dried in air at 550° C. for 4 hours.

Example 21: Preparation of the Catalyst U Based on 0.25% Nb/0.5% Ta/SiO$_2^\beta$ (0.25% by Weight of Nb and 0.5% by Weight of Ta in Relation to the Silica Mass) that is Obtained Via the Metallo-Organic Modern Sol-Gel Path (for Comparison Purposes)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. A solution that contains 0.13 g of niobium ethoxide (Nb(OCH$_2$CH$_3$)$_5$), 0.25 g of tantalum ethoxide (Ta(OCH$_2$CH$_3$)$_5$), 5 ml of ethanol and 0.4 ml of 68% (by volume) nitric acid is then added drop by drop under inert conditions to the preceding mixture. 50 ml of a 14% (by volume) ammonia solution is then added. The system is disturbed, and a gel forms. 19 ml of ethanol is then added to make possible an additional stirring for 3 hours. The final gel is filtered, washed with ethanol, and then dried at 100° C. for 24 hours. The catalyst U is obtained by calcination of the solid that is dried in air at 550° C. for 4 hours.

Example 22: Preparation of the Catalyst V Based on 10% Ta/SiO$_2$$^\beta$ (10% by Weight of Ta in Relation to the Silica Mass) that is Obtained Via the Metallo-Organic Modern Sol-Gel Path (for Comparison Purposes)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 3.31 g of tantalum ethoxide (Ta(OCH$_2$CH$_3$)$_5$) is then added drop by drop under inert conditions to the preceding mixture. 50 ml of a 14% (by volume) ammonia solution is then added. The system is disturbed, and a gel forms. 19 ml of ethanol is then added to make possible an additional stirring for 3 hours. The final gel is filtered, washed with ethanol, and then dried at 100° C. for 24 hours. The catalyst X is obtained by calcination of the solid that is dried in air at 550° C. for 4 hours.

Example 23: Preparation of the Catalyst W Based on 7% Nb/SiO$_2$$^\beta$ (10% by Weight of Ta in Relation to the Silica Mass) that is Obtained Via the Metallo-Organic Modern Sol-Gel Path (for Comparison Purposes)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. 3.37 g of niobium ethoxide (Nb(OCH$_2$CH$_3$)$_5$) is then added drop by drop under inert conditions to the preceding mixture. 50 ml of a 14% (by volume) ammonia solution is then added. The system is disturbed, and a gel forms. 19 ml of ethanol is then added to make possible an additional stirring for 3 hours. The final gel is filtered, washed with ethanol, and then dried at 100° C. for 24 hours. The catalyst X is obtained by calcination of the solid that is dried in air at 550° C. for 4 hours.

Example 24: Preparation of the Catalyst X Based on 7% Nb/10% Ta/SiO$_2$$^\beta$ (7% by Weight of Nb and 10% by Weight of Ta in Relation to the Silica Mass) that is Obtained Via the Metallo-Organic Modern Sol-Gel Path (Outside of the Invention)

12.5 ml of a 68% (by volume) nitric acid solution is added to a solution that contains 55 ml of tetraethyl orthosilicate (TEOS, Si(OCH$_2$CH$_3$)$_4$) and 150 ml of ethanol at ambient temperature. The whole mixture is left to stir for 30 minutes. A solution that contains 3.37 g of niobium ethoxide (Nb (OCH$_2$CH$_3$)$_5$), 3.31 g of tantalum ethoxide (Ta(OCH$_2$CH$_3$)$_5$), 20 ml of ethanol and 1.6 ml of 68% (by volume) nitric acid is then added drop by drop under inert conditions to the preceding mixture. 50 ml of a 14% (by volume) ammonia solution is then added. The system is disturbed, and a gel forms. 19 ml of ethanol is then added to make possible an additional stirring for 3 hours. The final gel is filtered, washed with ethanol, and then dried at 100° C. for 24 hours. The catalyst X is obtained by calcination of the solid that is dried in air at 550° C. for 4 hours.

Example 25: Preparation of the Catalyst Y Based on 5% Zn/1% Ta/SiO$_2$$^\alpha$ (5% by Weight of Zn and 1% by Weight of Ta in Relation to the Silica Mass) that is Obtained by Successive Dry Impregnations of Zinc and Tantalum Precursors that are Attached to the Surface of the Davisil 636 Commercial Silica ($\alpha$) (for Comparison Purposes)

11.37 g of hexahydrated zinc nitrate is diluted in 80 ml of water. This solution is quickly added drop by drop and mixed with 50 g of the Davisil 636 silica (SBET$\approx$500 m$^2$/g, Vp$\approx$0.9 ml/g and $\phi\approx$7 nm, granulometry: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

0.67 g of tantalum ethoxide (Ta(OCH$_2$CH$_3$)$_5$) is diluted in 48 ml of ethanol. This solution is quickly added drop by drop and mixed with 30 g of the solid that was previously prepared until wettability of the surface of the latter (dry impregnation) is observed. The solid is then placed in an ethanol-saturated atmosphere for 3 hours, dried at 100° C. for 24 hours. The catalyst V is obtained by calcination of the solid that is dried in air at 550° C. for 4 hours.

Example 26: Preparation of the Catalyst Z Based on 5% Zn/0.25% Nb/SiO$_2$$^\alpha$ (5% by Weight of Zn and 0.25% by Weight of Nb in Relation to the Silica Mass) that is Obtained by Successive Dry Impregnations of the Zinc and Tantalum Precursors that are Attached to the Surface of the Davisil 636 Commercial Silica ($\alpha$) (for Comparison Purposes)

11.37 g of hexahydrated zinc nitrate is diluted in 80 ml of water. This solution is quickly added drop by drop and mixed with 50 g of the Davisil 636 silica (SBET$\approx$500 m$^2$/g, Vp$\approx$0.9 ml/g and $\phi\approx$7 nm, granulometry: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

0.53 g of niobium oxalate and pentahydrated ammonium oxalate is diluted in 80 ml of water. This solution is quickly added drop by drop and mixed with 50 g of the solid that was previously prepared until wettability of the surface of the latter (dry impregnation) is observed. The solid is then placed in a water-saturated atmosphere for 3 hours, dried at 100° C. for 24 hours. The catalyst W is obtained by calcination of the solid that is dried in air at 550° C. for 4 hours.

Example 27: Preparation of the Catalyst AA Based on 10% Zn/0.25% Nb/1% Ta/SiO$_2$$^\alpha$ (10% by Weight of Zn, 0.25% Nb and 1% by Weight of Ta in Relation to the Silica Mass) that is Obtained by Successive Dry Impregnations of the Zinc, Niobium and Tantalum Precursors that are Attached to the Surface of the Davisil 636 Commercial Silica ($\alpha$) (According to the Invention)

22.74 g of hexahydrated zinc nitrate is diluted in 80 ml of water. This solution is quickly added drop by drop and mixed with 50 g of the Davisil 636 silica (SBET$\approx$500 m$^2$/g, Vp$\approx$0.9 ml/g and $\phi\approx$7 nm, granulometry: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

0.53 g of niobium oxalate and pentahydrated ammonium oxalate is diluted in 76 ml of water. This solution is quickly added drop by drop and mixed with 50 g of the previously prepared solid until wettability of the surface of the latter (dry impregnation) is observed. The solid is then placed in a water-saturated atmosphere for 3 hours, dried at 100° C. for 24 hours. The intermediate solid is obtained by calcination of the solid that is dried in air at 550° C. for 4 hours.

0.67 g of tantalum ethoxide ($Ta(OCH_2CH_3)_5$) is diluted in 45 ml of ethanol. This solution is quickly added drop by drop and mixed with 30 g of the previously prepared solid until wettability of the surface of the latter (dry impregnation) is observed. The solid is then placed in an ethanol-saturated atmosphere for 3 hours, dried at 100° C. for 24 hours. The catalyst X is obtained by calcination of the solid that is dried in air at 550° C. for 4 hours.

Example 28: Preparation of the Catalyst AB Based on 10% Zn/1.7% Ta/$SiO_2^\alpha$ (10% by Weight of Zn and 1.7% by Weight of Ta in Relation to the Silica Mass) that is Obtained by Successive Dry Impregnations of the Zinc and Tantalum Precursors that are Attached to the Surface of the Davisil 636 Commercial Silica ($\alpha$) (for Comparison Purposes)

22.74 g of hexahydrated zinc nitrate is diluted in 80 ml of water. This solution is quickly added drop by drop and mixed with 50 g of the Davisil 636 silica (SBET≈500 m$^2$/g, Vp≈0.9 ml/g and ϕ≈7 nm, granulometry: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

1.14 g of tantalum ethoxide ($Ta(OCH_2CH_3)_5$) is diluted in 48 ml of ethanol. This solution is quickly added drop by drop and mixed with 30 g of the previously prepared solid until wettability of the surface of the latter (dry impregnation) is observed. The solid is then placed in an ethanol-saturated atmosphere for 3 hours, dried at 100° C. for 24 hours. The catalyst Y is obtained by calcination of the solid that is dried in air at 550° C. for 4 hours.

Example 29: Preparation of the Catalyst AC Based on 10% Zn/0.5% Nb/0.8% Ta/$SiO_2^\alpha$ (10% By Weight of Zn, 0.5% by Weight of Nb and 0.8% By Weight of Ta in Relation to the Silica Mass) that is Obtained by Successive Dry Impregnations of the Niobium, Zinc and Tantalum Precursors that are Attached to the Surface of the Davisil 636 Commercial Silica ($\alpha$) (According to the Invention)

22.74 g of hexahydrated zinc nitrate is diluted in 80 ml of water. This solution is quickly added drop by drop and mixed with 50 g of the Davisil 636 silica (SBET≈500 m$^2$/g, Vp≈0.9 ml/g and ϕ≈7 nm, granulometry: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

1.06 g of niobium oxalate and pentahydrated ammonium oxalate is diluted in 76 ml of water. This solution is quickly added drop by drop and mixed with 50 g of the previously prepared solid until wettability of the surface of the latter (dry impregnation) is observed. The solid is then placed in a water-saturated atmosphere for 3 hours, dried at 100° C. for 24 hours. The intermediate solid is obtained by calcination of the solid that is dried in air at 550° C. for 4 hours.

0.54 g of tantalum ethoxide ($Ta(OCH_2CH_3)_5$) is diluted in 48 ml of ethanol. This solution is quickly added drop by drop and mixed with 30 g of the previously prepared solid until wettability of the surface of the latter (dry impregnation) is observed. The solid is then placed in an ethanol-saturated atmosphere for 3 hours, dried at 100° C. for 24 hours. The catalyst Y is obtained by calcination of the solid that is dried in air at 550° C. for 4 hours.

Example 30: Preparation of the Catalyst AD Based on 10% Zn/0.2% Nb/1.4% Ta/$SiO_2^\alpha$ (10% by Weight of Zn, 0.2% by Weight of Nb and 1.4% by Weight of Ta in Relation to the Silica Mass) that is Obtained by Successive Dry Impregnations of the Niobium, Zinc and Tantalum Precursors that are Attached to the Surface of the Davisil 636 Commercial Silica ($\alpha$) (According to the Invention)

22.74 g of hexahydrated zinc nitrate is diluted in 80 ml of water. This solution is quickly added drop by drop and mixed with 50 g of the Davisil 636 silica (SBET≈500 m$^2$/g, Vp≈0.9 ml/g and ϕ≈7 nm, granulometry: 200-500 microns) until wettability of the surface of the latter (dry impregnation) is observed. The solid is then placed in a water-saturated atmosphere for 3 hours, dried at 100° C. for 24 hours. The intermediate solid is obtained by calcination of the solid, which is dried damp (20% water) at 550° C. for 4 hours.

0.42 g of niobium oxalate and pentahydrated ammonium oxalate is diluted in 76 ml of water. This solution is quickly added drop by drop and mixed with 50 g of the previously prepared solid until wettability of the surface of the latter (dry impregnation) is observed. The solid is then placed in a water-saturated atmosphere for 3 hours, dried at 100° C. for 24 hours. The intermediate solid is obtained by calcination of the solid that is dried in air at 550° C. for 4 hours.

0.95 g of tantalum ethoxide ($Ta(OCH_2CH_3)_5$) is diluted in 48 ml of ethanol. This solution is quickly added drop by drop and mixed with 30 g of the previously prepared solid until wettability of the surface of the latter (dry impregnation) is observed. The solid is then placed in an ethanol-saturated atmosphere for 3 hours, dried at 100° C. for 24 hours. The catalyst Y is obtained by calcination of the solid that is dried in air at 550° C. for 4 hours.

Definition of the Terms pph ($g/g_{cat}/h$):

$$pph = \frac{\text{mass flow rate of the feedstock (g/h)}}{\text{catalyst mass (gcat)}}$$

Conversion (% by weight):

$$\text{conversion} = 100 * \left(1 - \frac{\text{mass flow rate of exiting ethanol} + \text{mass flow rate of exiting acetaldehyde}}{\text{mass flow rate of entering ethanol} + \text{mass flow rate of entering acetaldehyde}}\right)$$

Productivity ($g_c/g_{cat}/h$)

$$productivity = \frac{\text{mass flow rate of carbon belonging to butadiene (gc/h)}}{\text{catalyst mass (gcat)}}$$

Selectivity (% C):

$$selectivity = \frac{\text{mass flow rate of carbon belonging to butadiene (gc/h)}}{\text{mass flow rate of carbon belonging to the converted feedstock}}$$

{A+B} represents the weighted activity of the catalysts A and B in the absence of any interaction between these two catalysts.

$$pph\{A + B\} = pph(A) + pph(B)$$

$$productivity\{A + B\} = productivity(A) + productivity(B)$$

$$selectivity\{A + B\} = \frac{productivity(A) * selectivity(A) + productivity(B) * selectivity(B)}{productivity(A) + productivity(B)}$$

If a better result is obtained during the combination of A and B, synergetic interaction may be said to have taken place. If a less good result is obtained, this is an antagonistic interaction.

Description of the Catalytic Test Unit

The reactor that is used in the following examples consists of a stainless steel tube that is 20 cm long and 10 mm in diameter. The reactor is first loaded with carborundum and then with the catalyst that is diluted in carborundum and finally with carborundum. The carborundum is inert relative to the feedstock and does not influence the catalytic results; it makes it possible to position the catalyst in the isothermal zone of the reactor and to limit the risks of material and heat transfer problems. The temperature of the reactor is controlled with a tubular furnace with three heating zones. The liquid feedstock (mixture of ethanol and acetaldehyde in a ratio R) is injected via a double-piston HPLC pump. The liquid stream is evaporated in the lines that are heated by a tracer before entering into the reactor and is homogenized by passing into a static mixer. The products that are formed during the reaction are kept in the vapor phase so that they can be analyzed on-line by gas chromatography (PONA and Carboxen 1010 capillary columns) to make possible the most precise identification of the hundreds of products formed. The catalyst is activated in situ under nitrogen at the test temperature. The specific operating conditions are described in the following examples.

Catalytic Test 1: Demonstration of the Nb/Ta Synergy Effect—EtOH/AcH Feedstock

In this test, the ethanol/acetaldehyde ratio is set at 2.6 (mol/mol), the temperature at 350° C., and the pressure at 1.5 bar. For each catalyst, the pph and therefore the feedstock flow rate are adjusted to obtain a conversion of the feedstock of 35%.

The values of carbon productivity and butadiene selectivity are measured at this operating point.

|  | Catalyst | Ta Content | Nb Content | pph (g/$g_{cat}$/h) | Butadiene Productivity ($g_C/g_{cat}$/h) | Selectivity (% C) |
|---|---|---|---|---|---|---|
|  | A | 0.5 | — | 0.9 | 0.11 | 68 |
|  | B | — | 0.5 | 0.9 | 0.10 | 61 |
|  | {A + B} | 0.5 | 0.5 | 1.8 | 0.21 | 65 |
| Outside of the Invention | C | 0.5 | 0.5 | 2.0 | 0.26 | 73 |
| Outside of the Invention | D | 0.5 | 0.5 | 1.7 | 0.22 | 73 |
| According to the Invention | E | 0.5 | 0.5 | 3.0 | 0.39 | 74 |
| Outside of the Invention | F | 0.5 | 0.25 | 1.6 | 0.21 | 74 |

The catalyst E according to the invention has a selectivity and a productivity that are greater than those of the catalysts outside of the invention.

|  | Catalyst | Ta Content | Nb Content | pph (g/$g_{cat}$/h) | Butadiene Productivity ($g_C/g_{cat}$/h) | Selectivity (% C) |
|---|---|---|---|---|---|---|
|  | A | 0.5 | — | 0.9 | 0.11 | 68 |
|  | B" | — | 1 | 1.9 | 0.20 | 59 |
|  | {A + B"} | 0.5 | 1 | 2.8 | 0.31 | 63 |
| Outside of the Invention | F' | 0.5 | 1 | 2.0 | 0.24 | 67 |
| Outside of the Invention | F" | 0.5 | 1 | 2.0 | 0.26 | 67 |

The catalyst F' with a niobium content that is greater than that of tantalum does not make it possible to improve selectivity and productivity in comparison to the sum of the performances of the catalysts A and B", even by modifying the order of addition of tantalum and niobium (F").

Catalytic Test 2: Demonstration of the Nb/Ta Synergy Effect—EtOH/AcH Feedstock

In this test, the ethanol/acetaldehyde ratio is set at 2.6 (mol/mol), the temperature at 350° C. and the pressure at 1.5 bar. For each catalyst, the pph and therefore the feedstock flow rate are adjusted to obtain a conversion of the feedstock of 25%.

The values of carbon productivity and butadiene selectivity are measured at this operating point.

The feedstock flow rate is regulated to obtain a conversion of the feedstock of 25%.

|  | Catalyst | Ta Content | Nb Content | pph (g/$g_{cat}$/h) | Butadiene Productivity ($g_C/g_{cat}$/h) | Selectivity (% C) |
|---|---|---|---|---|---|---|
|  | H | 0.5 | — | 1.7 | 0.16 | 70 |
|  | I | — | 0.5 | 2.7 | 0.20 | 53 |
|  | {H + I}$_{50/50}$ | 0.5 | 0.5 | 4.4 | 0.36 | 61 |
| According to the Invention | J | 0.5 | 0.5 | 9.5 | 1.02 | 71 |
| According to the Invention | J' | 0.5 | 0.5 | 6.8 | 0.75 | 73 |

The catalysts J and J' according to the invention have a selectivity and a productivity that are greater than those of the catalysts H and I.

|  | Catalyst | Ta Content | Nb Content | pph (g/g$_{cat}$/h) | Butadiene Productivity (g$_C$/g$_{cat}$/h) | Selectivity (% C) |
|---|---|---|---|---|---|---|
|  | V | 10 | — | 25 | 2.35 | 71 |
|  | W | — | 7 | 20 | 1.06 | 40 |
|  | {V + W} | 10 | 7 | 45 | 3.41 | 61 |
| Outside of the Invention | X | 10 | 7 | 32 | 2.37 | 56 |

The catalyst X with a niobium content that is greater than 6% does not make it possible to improve selectivity and productivity in comparison to the sum of performances of the catalysts V and W.

Catalytic Test 3: Demonstration of the Absence of Ta/Zr Synergy—EtOH/AcH Feedstock In this test, the ethanol/acetaldehyde ratio is set at 2.6 (mol/mol), the temperature at 350° C. and the pressure at 1.5 bar. For each catalyst, the pph and therefore the feedstock flow rate are adjusted to obtain a conversion of the feedstock of 35%.

The values of carbon productivity and butadiene selectivity are measured at this operating point.

|  | Catalyst | Ta Content | Zr Content | pph (g/g$_{cat}$/h) | Butadiene Productivity (g$_C$/g$_{cat}$/h) | Selectivity (% C) |
|---|---|---|---|---|---|---|
|  | A | 0.5 | — | 0.9 | 0.11 | 68 |
|  | N | — | 0.5 | 2.4 | 0.28 | 64 |
|  | {A + N} | 0.5 | 0.5 | 3.3 | 0.39 | 65 |
| Outside of the Invention | O | 0.5 | 0.5 | 1.9 | 0.25 | 65 |

In contrast to the tantalum/niobium association, the association between tantalum and zirconium does not make it possible to improve the selectivity of the reaction and even has an antagonistic effect on the productivity of the catalyst.

Catalytic Test 4: Demonstration of the Absence of Nb/Zr Synergy—EtOH/AcH Feedstock In this test, the ethanol/acetaldehyde ratio is set at 2.6 (mol/mol), the temperature at 350° C. and the pressure at 1.5 bar. For each catalyst, the pph and therefore the feedstock flow rate are adjusted to obtain a conversion of the feedstock of 35%.

The values of carbon productivity and butadiene selectivity are measured at this operating point.

The feedstock flow rate is regulated to obtain a conversion of the feedstock of 35%.

|  | Catalyst | Nb Content | Zr Content | pph (g/g$_{cat}$/h) | Butadiene Productivity (g$_C$/g$_{cat}$/h) | Selectivity (% C) |
|---|---|---|---|---|---|---|
|  | B″ | 1 | — | 1.8 | 0.20 | 59 |
|  | N | — | 0.5 | 2.2 | 0.28 | 64 |
|  | {B″ + N} | 1 | 0.5 | 4.2 | 0.48 | 62 |
| Outside of the Invention | P | 1 | 0.5 | 2.7 | 0.38 | 66 |
|  | B″ | 1 | — | 1.8 | 0.20 | 59 |
|  | N′ | — | 0.25 | 1.2 | 0.16 | 65 |
|  | {B″ + N′} | 1 | 0.25 | 3.0 | 0.36 | 62 |
| Outside of the Invention | P′ | 1 | 0.25 | 1.6 | 0.23 | 66 |

In contrast to the tantalum/niobium association, the association between niobium and zirconium makes it possible to improve the selectivity of the reaction, but it has an antagonistic effect on the productivity of the catalyst.

Catalytic Test 5: Demonstration of the Substitution Effect—EtOH/AcH Feedstock

In this test, the ethanol/acetaldehyde ratio is set at 2.6 (mol/mol), the temperature at 350° C., the pph at 2.5 h$^{-1}$ and the pressure at 1.5 bar. The values of carbon productivity and butadiene selectivity are measured at this operating point.

A standard curve of the relationship between the tantalum content and butadiene productivity is plotted by causing the tantalum content to vary between 0.25% and 5%, with the catalysts being prepared by following the preparation protocol for the catalyst A. This curve is presented in FIG. 1.

The curve that is presented in FIG. 1 makes it possible, according to the productivity that is obtained under the test conditions with each catalyst based on Ta and Nb, to estimate the tantalum content that would be necessary to obtain this productivity if a catalyst containing only Ta was used. The amount of tantalum saved represents the difference between this value and the actual tantalum content of the tested catalyst.

| Catalyst | Ta Content | Nb Content | Conversion (% by Weight) | Butadiene Productivity (g/g$_{cat}$/h) | Selectivity (% C) | Equivalent of Ta by Itself (Depending on Production) | Ta Saved g/g$_{cat}$ (% Ta) |
|---|---|---|---|---|---|---|---|
| C | 0.5 | 0.5 | 31 | 0.31 | 73 | 1 | 0.5 (49%) |
| D | 0.5 | 0.5 | 29 | 0.28 | 72 | 0.9 | 0.4 (41%) |
| E | 0.5 | 0.5 | 37 | 0.36 | 74 | 1.4 | 0.9 (62%) |
| R | 2 | 0.5 | 47 | 0.43 | 72 | 2.3 | 0.3 (9%) |

The table shows that it is possible to obtain the same performances as a catalyst that is based on tantalum with catalysts based on niobium and tantalum, but with smaller contents of tantalum. The catalyst E that is prepared by introducing in succession the niobium element and then the tantalum element makes it possible to achieve a much more significant savings in tantalum.

Catalytic Test 6: Demonstration of the Substitution Effect— EtOH/AcH Feedstock

In this test, the ethanol/acetaldehyde ratio is set at 2.6 (mol/mol), the temperature at 350° C., the pph at 3 $h^{-1}$ and the pressure at 1.4 bar. The values of carbon productivity and butadiene selectivity are measured at this operating point.

|  | Catalyst | Ta Content | Nb Content | Conversion (% by Weight) | Butadiene Productivity ($g/g_{cat}/h$) | Selectivity (% C) |
|---|---|---|---|---|---|---|
|  | S | 0.75 | — | 29 | 0.34 | 71 |
| According to the Invention | T | 0.5 | 0.25 | 32 | 0.37 | 70 |
| Outside of the Invention | U | 0.5 | 0.25 | 28 | 0.34 | 73 |

The table shows that it is possible to obtain the same performances as a catalyst that is based on tantalum with catalysts based on niobium and tantalum but with smaller contents of tantalum, the catalyst prepared by introducing consecutively the niobium and then the tantalum making possible a significant gain in productivity in relation to the catalyst U in which tantalum and niobium have been added simultaneously.

Catalytic Test 7: Demonstration of the Synergy Effect— EtOH Feedstock

In this test, the feedstock contains only ethanol, the temperature is set at 375° C., and the pressure at 1.4 bar. For each catalyst, the pph and therefore the feedstock flow rate are adjusted to obtain a conversion of the feedstock of 55%.

The values of carbon productivity and butadiene selectivity are measured at this operating point.

|  | Catalyst | Zn Content | Ta Content (% by Weight) | Nb Content (% by Weight) | pph | Butadiene Productivity (g/gcat/h) | Selectivity (% C) |
|---|---|---|---|---|---|---|---|
|  | V | 5 | 1 | 0 | 0.5 | 0.11 | 63 |
|  | W | 5 | 0 | 0.25 | 0.2 | 0.03 | 45 |
|  | {V + W} | 10 | 1 | 0.25 | 0.7 | 0.14 | 59 |
| According to the Invention | X | 10 | 1 | 0.25 | 0.8 | 0.18 | 64 |

The catalyst X according to the invention has a selectivity and a productivity that are greater than those of the catalysts V and W.

Catalytic Test 8: Demonstration of the Substitution Effect— EtOH Feedstock

In this test, the feedstock contains only ethanol, the temperature is set at 350° C., the pph at 3 $h^{-1}$ and the pressure at 1.4 bar. The values of carbon productivity and butadiene selectivity are measured at this operating point.

|  | Catalyst | Zn Content | Ta Content (% by Weight) | Nb Content (% by Weight) | Conversion (% by Weight) | Butadiene Productivity (g/gcat/h) | Selectivity (% C) |
|---|---|---|---|---|---|---|---|
|  | Y | 10 | 1.7 | — | 55 | 0.34 | 63 |
| According to the Invention | Z | 10 | 0.8 | 0.5 | 53 | 0.29 | 61 |
| According to the Invention | Z' | 10 | 1.4 | 0.2 | 55 | 0.30 | 63 |

The table shows that it is possible within the framework of a method for producing butadiene in one step from ethanol to obtain the same performances as a catalyst based on tantalum with catalysts based on niobium and tantalum but with smaller contents of tantalum.

The invention claimed is:

1. A catalyst comprising a mesoporous oxide matrix, said matrix comprising at least one oxide of an element X that is silicon or titanium, alone or in a mixture, said catalyst comprising tantalum and niobium, having a tantalum mass of 0.1 to 30% of the mass of the mesoporous oxide matrix, a niobium mass of 0.02 to 6% of the mass of the mesoporous oxide matrix, the content by mass of the tantalum element in said catalyst being greater than or equal to the content by mass of the niobium element in said catalyst, said catalyst being prepared by consecutive introduction of the niobium element and then the tantalum element.

2. The catalyst according to claim 1, in which said oxide matrix is mesostructured.

3. The catalyst according to claim 1, in which said oxide matrix is a silicon oxide that has a specific surface area of 100 to 1,200 $m^2/g$, a mesopore volume of between 0.2 and 1.8 ml/g and a mesopore diameter of between 4 and 50 nm.

4. The catalyst according to claim 3, in which said oxide matrix contains an alkaline metal content that is expressed in terms of % by weight of metal in relation to the mass of the mesoporous matrix of less than 1% by weight.

5. The catalyst according to claim 1, further comprising at least one element of groups 1, 2, 3, 4 of the periodic table, or mixtures thereof, with the mass of said element representing between 0.01 and 5% of the mass of said mesoporous oxide matrix.

6. The catalyst according to claim 5, further comprising at least one element of groups 1 or 2 of the periodic table, or mixtures thereof, with the mass of said element representing between 0.01 and 5% of the mass of said mesoporous oxide matrix.

7. The catalyst according to claim 6, comprising at least one element that is Cs, Ca, Ba, or mixtures thereof, with the mass of said element representing between 0.01 and 5% of the mass of said mesoporous oxide matrix.

8. The catalyst according to claim 1, further comprising at least one element of groups 11 or 12 of the periodic table, or mixtures thereof, with the mass of said element representing between 0.5 and 10% of the mass of said mesoporous oxide matrix.

9. The catalyst according to claim 8, comprising at least Zn, with the mass of Zn representing between 0.5 and 10% of the mass of said mesoporous oxide matrix.

10. A process for the production of 1,3-butadiene from a feedstock that comprises at least ethanol, comprising contacting said feedstock with a catalyst according to claim 1, at a temperature of between 300 and 400° C., a pressure of between 0.15 and 0.5 MPa, and a volumetric flow rate of between 0.5 and 5 $h^{-1}$.

11. The process according to claim 10, in which the temperature is between 320° C. and 380° C.

12. The process according to claim 10, in which the pressure is between 0.15 and 0.3 MPa.

13. The process according to claim 10, in which the volumetric flow rate is between 1 and 4 $h^{-1}$.

* * * * *